United States Patent [19]

Spina et al.

[11] 4,191,176
[45] * Mar. 4, 1980

[54] INTRALENTICULAR CATARACT SURGERY

[75] Inventors: Joseph Spina, Bryn Mawr, Pa.; Michael K. Weibel, Redding, Conn.

[73] Assignee: Novo Laboratories, Inc., Wilton, Conn.

[*] Notice: The portion of the term of this patent subsequent to Mar. 14, 1995, has been disclaimed.

[21] Appl. No.: 827,100

[22] Filed: Aug. 23, 1977

Related U.S. Application Data

[63] Continuation-in-part of Ser. No. 771,551, Feb. 24, 1977, abandoned, which is a continuation-in-part of Ser. No. 660,873, Feb. 24, 1976, Pat. No. 4,078,564.

[51] Int. Cl.$^2$ ............................................. A61M 5/00
[52] U.S. Cl. ..................... 128/1 R; 128/216; 424/94
[58] Field of Search ............... 128/1, 213, 213 A, 215, 128/249, 216

[56] References Cited

U.S. PATENT DOCUMENTS

| | | | |
|---|---|---|---|
| 3,320,131 | 5/1967 | Smith | 424/94 |
| 3,589,363 | 6/1971 | Banko | 128/276 |
| 3,683,069 | 8/1972 | Hooreman | 424/94 |
| 4,078,564 | 3/1978 | Spina et al. | 128/216 |

OTHER PUBLICATIONS

Preparation and Properties of Water-Insoluble Derivatives of Trypsin-Atha Ban-Eli & Epraim Katchalaski, Journal of Biol. Research Chemistry, vol. No. 5, May 1963, pp. 1690-1698.

*Primary Examiner*—Robert W. Michell
*Assistant Examiner*—Milford Juten
*Attorney, Agent, or Firm*—Fidelman, Wolffe & Waldron

[57] ABSTRACT

An enzymatic intralenticular cataract treatment for removal of nuclear cortical and subcapsular regions of the cataractous lens through enzymatic digestion thereof which comprises introduction of a concentrated solution of a trypsin enzyme into the nuclear and cortical regions of a cataractous lens, and after enzymatic digestion removing the liquefied cataractous material. The procedure allows subsequent removal of the nuclear, cortical and subcapsular portions of a cataractous lens through a very tiny incision in the eye and lens capsule, leaving all other structures within the eye intact. Bovine and porcine trypsins are preferred.

7 Claims, 3 Drawing Figures

INTRALENTICULAR CATARACT SURGERY

This application is a continuation-in-part of Ser. No. 771,551 filed Feb. 24, 1977 now abandoned which in turn is a continuation-in-part of Ser. No. 660,873 filed Feb. 24, 1976, now U.S. Pat. No. 4,078,564.

BACKGROUND OF THE INVENTION

I. Field of the Invention

This invention lies in the field of cataract surgery and in particular relates to the enzymatic treatment of cataracts followed by removal of the enzymatically digested cataractous material.

II. Background

The lens is an optically clear encapsulated disc-like structure which is suspended within the eye, behind the iris and in front of the vitreous. It supplies part of the optical refracting power of the eye. The lens becomes cataractous when its nuclear and/or cortical and/or subcapsular regions become opaque, thus blocking the path of light entering the eye, thereby causing diminished vision. A cataractous lens (hereinafter identified as cataract) is simply a lens that has become cloudy.

For further background to this invention and for more detailed discussion of the rationale of liquefying a lens enzymatically, reference is made to Ser. No. 660,873 filed Feb. 24, 1973. Suffice it to point out here that surgical techniques for removing cataracts are not entirely satisfactory to patient and surgeons.

The object of this invention is to provide a procedure which eliminates much, if not all, of the hazards and trauma involved in the heretofore known surgical procedures for removing cataracts.

A further object of this invention is to provide certain active proteinases capable of enzymatic digestion of cataractous lens tissue in vivo.

SUMMARY OF THE INVENTION

This invention provides a procedure for intralenticular cataract therapy which involves introduction of a concentrated trypsin solution into throughout the nuclear, cortical and subcapsular regions of a cataractous lens. After a suitable period of time, e.g. 12–96 hours, the enzyme digested cataractous lens material is easily removed by aspiration and irrigation techniques in an atraumic manner. The bovine and porcine trypsins are herein contemplated as preferred.

RATIONALE OF THE INVENTION

The invention takes advantage of a unique physiological situation within the lens itself. During the embryonic stages of human development the lens material is isolated from the rest of the body and develops independent of the organism as a whole to such an extent that every human will react to the contents of his or her lens as if it were a foreign protein. In the adult human, the lens is surrounded by the lens capsule which is primarily a collagenous structure. This capsule or bag actually isolates the lens within the body to such an extent that exogenous enzymes may be introduced into the lens without creating immunologic foreign protein responses thereto.

Technological advances have made available to the surgeon both equipment and techniques for operating on the lens itself. Conventional surgical equipment, including for example the operating microscope that has gone into wide spread use in the past fifteen years now enable the surgeon to discern anatomical details that previously were too small for direct visualization by the unaided eye. In addition, the availability of micro cannulae make it possible for a surgeon to enter a structure as small as the human lens (approximately 9 mm in diameter) without doing major damage thereto. In total, the operating techniques and the surgical equipment required for surgery on the lens itself are available to the art, forming no part of this invention and will not be described herein (aside from allusions thereto when exemplary preferred embodiments of practice of this invention are provided).

Within the art of intraocular ophthalmic surgical procedures for conventional intracapsular cataract removal, the use of an exogenous enzyme to facilitate the removal of an intact lens is established. A well characterized proteolytic enzyme, $\alpha$-chymotrypsin, has been used to soften the suspensory ligaments of the zonular region which attach the lens capsule to the ciliary muscle. (As is well known in the art $\alpha$-chymotrypsin is not a trypsin).

Also the use of an exogenous enzyme, fibrinolysin, to assist the degradation of blood clots within the eye is established within the art of ophthalmic intraocular surgery.

Furthermore, there is an established precedent in the medical arts for use of digestive enzymes as an aid in necrotic tissue removal for wound debridement procedures.

In the treatment of congenital cataracts, too firm to be aspirated using a simple needle and syringe, some eye surgeons have believed that incision of the anterior capsule permits the enzymes of the aqueous humor to permeate the firm nuclear tissue, and then within a few days the cataract softens to the extent that it can be aspirated easily. This procedure does not work for hard, senile cataracts because of low peripheral permeability associated with their dense and compact nature.

It has now been discovered that compact lens tissue can be treated by a trypsin so as to soften the lens sufficiently to allow its removal by aspiration and irrigation techniques.

EXPLANATION OF THE INVENTION

For further understanding of this invention, reference is now made to the attached drawing, wherein:

FIG. 1 diagrammatically illustrates a cannula inserted in the lens of an eye,

Figure 3:
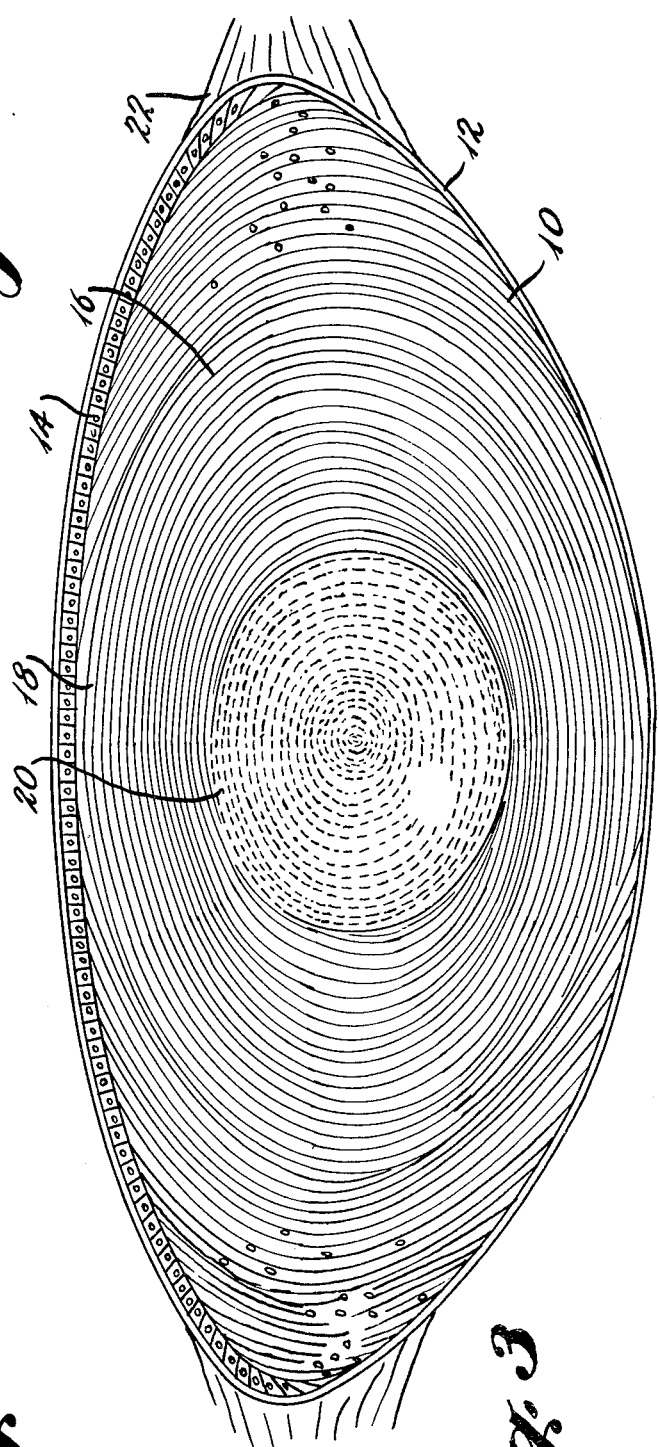
FIG. 3 is an enlarged diagrammatic cross-section of the human lens capsule and its contents.

Referring now to FIG. 3, it may be seen how the lens 10 is divided up into capsule 12 epithelium 14 and lens substance 16 which consists of lens fiber. The lens substance can be further described as made up of the cortex 18, the cortex being layers of relatively soft fibers which lie directly beneath the capsule 12, and the nucleus, the nucleus 20 being the hard, closely packed cells at the center of the lens. Extending into lens 10 at the sides thereof are the zonules 22, the zonules being the suspensatory ligaments which retain the lens in place inside the eye.

Any exogenous material inserted into the lens can be physically compartmentalized within the lens substance 16 for an extended period by the lens capsule 12, provided first that the introduction technique does not rupture or physically destroy the lens capsule and second that the exogenous material does not digest the capsule to a destructive degree. Significant to practice of this invention is that lens capsule 12 has a biochemical composition which is substantially different from that of cortex 18 and nucleus 20 of the main lens substance. Exogenous enzymes that are capable of selectively digesting the tissue of nucleus and cortex yet leave lens capsule 12 anatomically intact do exist. Parenthetically it may be noted that the macromolecular character of enzymes keeps them from permeating rapidly, if at all, through the reticular structure of the capsular membrane. Accordingly, selective enzymes introduced into the cortex and nucleus will become trapped therein, and over a period of time are capable of enzymatically degrading the senile lens substance.

Figure 1:
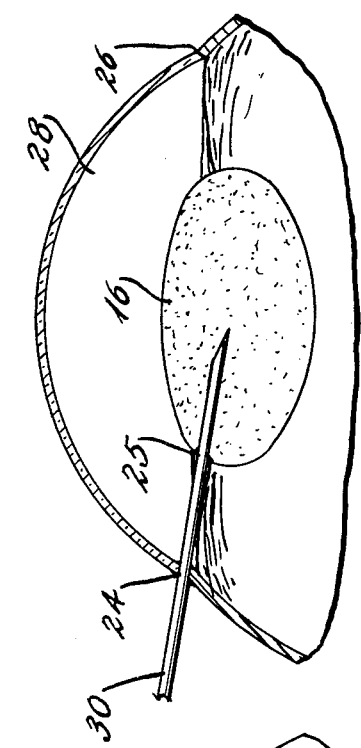

One exemplary mode of practicing the invention involves making a puncture 24 at the sclera or at the scleral-corneal juncture 26 large enough for a cannula or needle, as is illustrated in FIG. 1, following which a solution of trypsin is introduced into the lens. Thereafter the cannula track within the lens and the capsular puncture site are sealed, e.g. by an air bubble, and then sufficient time allowed for enzymatic digestion of the lens. Subsequently the by then softened or liquefied lens is removed by conventional aspiration and irrigation techniques or other (conventional) mechanical means, employing for example the techniques described in the medical literature for removing congenital or soft cataracts. Desirably, cataract removal is carried out by aspirating and irrigating through a small limbal opening similar to puncture opening 24.

As can be seen in FIG. 3, the lens fiber formed from differentiated epithelial cells in the nucleus 20 and cortex 18 regions inside the lens capsule, are layered (somewhat like an onion) so that any enzyme containing liquid forced into the lens substance 16 permeates the entire lens largely along the lines of disjunction formed at the interfaces of various generations of lens fibers. In terms of practicing this invention the layered structure of the lens allows virtually all portions of the nucleus and cortex to come into immediate or eventual contact with the trypsin. A normal senile cataract can accommodate up to 20 microliters of liquid without increasing the intralenticular pressure to a level where rupture of the capsule 12 occurs. Accordingly, introduction of a concentrated solution of exogenous enzymes directly into the lens according to practice of this invention focuses an enzymatic action exclusively upon cortical, nuclear and subcapsular cataractous tissue in vivo.

Degrading the cataract in situ as is herein contemplated imposes requirements for high levels of enzymatic unit activity and of selectivity. Fortuitously, highly selective enzymes exist. With high purity forms of enzymes, such as for example in crystalline enzymes, concentrated (aqueous) solutions of mixed enzymes can be formulated, for example 10% wt/wt solutions. Accordingly, the above described 20 microliter limit allows (in theory) introduction of as much as 2 mg of pure enzyme into the lens substance. Since a normal lens will weigh about 200 mg, the enzyme to lens substance wt. ratio of about 1:100 readily obtainable constitutes a high enzyme:substrate ratio particularly since the layered nature of the lens potentially allows all of the lens tissue ultimately to contact with the enzyme solution. Basically optimal enzyme concentrations are determined by the type of cataract and age of lens being treated. Rabbit studies indicate that trypsin concentrations of 0.1 mg/ml–10 mg/ml of trypsin will digest lens tissue. This concentration range is far below solubility limits for the enzyme yet constitutes a high enzyme to substrate ratio in the lens. Concentration of enzyme can be adjusted to preferences of the surgeon. For example, the enzyme concentration and total amount can be made low enough to digest the lens incompletely and mechanical removal of undigested fragments of the lens (nucleus or cortex) relied upon. On the other hand, the more concentrated enzyme solutions will digest the lens substance more rapidly and to a complete degree. During the course of the period allowed for digesting the lens substance, the proteinase undergoes a time dependant inactivation caused by autolysis thereof.

DETAILED PRACTICE OF THE INVENTION

Figure 2:
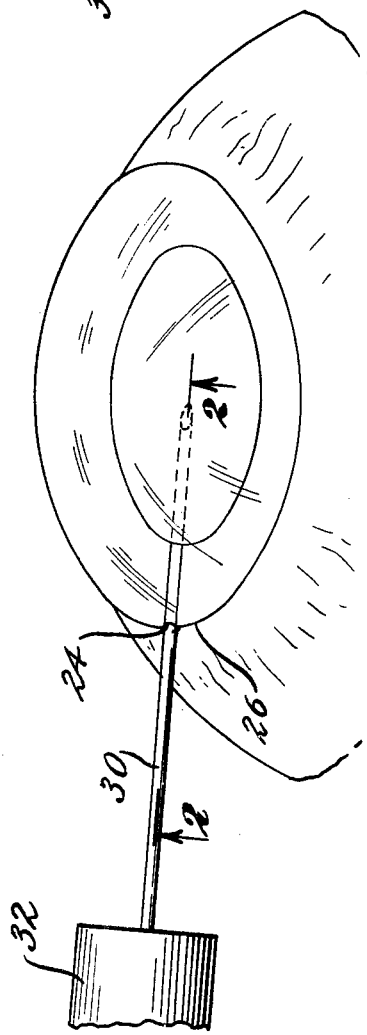
FIG. 2 is a cross-section taken along line 2—2 of FIG. 1.

The detailed practice of this invention can be appreciated in light of the drawing, notably of FIGS. 1 and 2. As can be seen therein, the lens degrading solution is delivered by a microcannula 30 attached to a suitable miniaturized liquid dispensing device such as a microliter syringe 32 from a limbal puncture directly into nucleus 20, introducing for example 6 microliters of a 0.05–0.5% w/v trypsin solution (0.5–5 mg/ml). The outside diameter of the microcannula for example may be approximately 20 microns, or as small as structural strength considerations permit. Large diameter cannulas tend to rent and/or rip the lens capsule during penetration thereof and substantially smaller diameter cannulas of stainless steel do not possess sufficient rigidity to cleanly penetrate into the lens substance. Use of a tracked micromanipulator to reduce lateral motion of the cannula upon entering the lens is recommended, but is not considered essential. With the aid of an operating microscope, a 200 micron microcannula can be adequately inserted into the center of the lens manually. However, restriction of lateral motion by the cannula once positioned in the lens is essential for maintaining a good seal about the needle track during delivery of the trypsin solution.

As has already been pointed out, the enzyme containing solution injected into the lens by a manual or pneumatic driven syringe system is an amount of fluid which can be accommodated by an average human lens, i.e. not more than about 20 microliters. The distribution pattern of the injected fluid may be observed by incorporating a soluble, inert dye such as fluorescein into the injection fluid in amounts of 0.01–1.0% w/v. Presence of the tracking indicator is considered important for satisfying surgeons that proper delivery and distribution pattern of enzyme into the lens is achieved.

In a preferred mode of enzyme introduction, injection of the solution into the central portion of the lens is followed by injection of a tiny air bubble or bubbles into the track of the cannula as the cannula is withdrawn from the lens and out of the eye. The air bubble or bubbles seal the small puncture site 25 in the lens capsule and thus block the egress of enzyme solution from the lens along the cannula track (before normal intralenticular pressure is restored).

The composition of the digestive mixture and the intralenticular incubation time can be adjusted to achieve a high level of liquefaction or softening of the lens nuclear and cortical region. Termination of the lens liquefaction process and protection of other intraocular structures, in the event of escape of the enzymatic digestive agent from the lens capsule can be achieved by introduction of a specific enzyme inhibitor e.g. "Aprotinin" into the anterior chamber 28 of the eye.

Contemplated for practice of this invention is introduction of enzyme inhibitors into the anterior chamber 28 of the eye in the event of enzyme leakage thereinto, or even as a precaution against such leakage. High molecular weight (or macromolecular) inhibitors are preferred. They will not permeate into the lens capsule, and therefore, do not interfere with the enzymatic digestion of the lens cortex and nucleus.

Trypsin enzymes obtained from animal or microbial species, even those possessing substantial homology in primary structure, are seldom immunologically identical. Therefore, these (enzymes) proteins are potentially antigenetic in the human. Fortunately, the lens is not vascularized and due to presence of the lens capsule does not communicate with the immunological response machinery in mammals. Mature human lens proteins are themselves antigenic, indicating their early immunochemical isolation during embryogenic differentiation. Accordingly, introduction of the trypsin into the lens and containment therein does not cause adverse immunological reactions.

The enzyme mixture introduced into the lens will be a 0.1–10.0 mg/ml aqueous solution of crystalline trypsin, e.g. bovine or porcine trypsin, 0.5–5.0 mg/ml being preferred, desirably in saline or balanced salt solution buffered to pH 7–8. Crystalline ultra pure enzymes are, of course, preferred; but in practice, somewhat lower purity level enzymes can be used. However, high purity crystalline bovine and porcine trypsin are available in quantity (e.g. "Trypure").

After the concentrated 0.01–1.0% w/v trypsin solution has been introduced into the lens, a suitable digestion period is allowed to elapse. Such period might, for example, be 3 days and will depend upon enzyme concentration, the hardness of the cataractous lens, and even the preferences of the surgeon. Desirably, the lens will be softened or liquefied to the point where the residue can be easily irrigated and aspirated out or merely irrigated out through a small incision in the limbus. Partial liquefaction to a lesser degree such as size reduction and/or softening may satisfy the surgeon by allowing the senile cataract to be readily fragmented and then removed through a small incision opening. All in all, the enzyme concentration, the total quantity of liquid introduced into the lens, and digestion time may be varied to suit the requirements of the surgeon and the needs of the individual patient.

From the viewpoint of the patient and surgeon, surgical mishaps and consequent exposure of occular structures other than the lens to enzyme solution are readily corrected with trypsin because a potent pancreatic trypsin inhibitor, namely and preferably "Aprotinin," can be immediately introduced into the regions exposed to the enzyme.

Investigation of single source enzymes has established that many individual proteinases will liquefy human lens in vitro. For example, freshly removed human lenses were digested in vitro in a balanced salt solution pH 7.4 by enzymes concentrations of about 350 units/ml* with papain, Subtilisin Carsberg, "Pronase-P," "Savarase," "Alcalase," "Neutrase," "Esperase." In the instance of each enzyme, the lenses were degraded to a substantial extent, as evidenced by considerable reduction in lens size and often softening of the lens (residue).

*1 unit is defined as that amount of enzyme which produces 1 μmole of TCA soluble tyrosine per minute (measured by standard Folin-Ciocalteau method) employing caesin as the substrate. The experimental conditions are 0.6% wt/vol casein in 0.05 M $K_2HPO_4/KH_2PO_4$ pH 7.5 at 37° C.

The many diverse commercially-available proteinases that have degraded human lenses permit selection of a preferred proteinase based upon enzyme properties as a whole, i.e., activity to lens tissue, selectivity to lens tissue vis-a-vis other tissues and ease of inhibition. Thus, the enzymes preferred for practice of this invention are highly purified, desirably homogeneous or even monocomponent trypsin. It has been found that trypsin preferentially attacks the cortical and nuclear components of the lens relative to the lens capsule, and does not cause significant trauma to the other structures present in the anterior segment of the eye. Inert behavior to the lens capsule is desirable, because then all enzyme introduced into the lens becomes compartmentalized from the posterior segment and from eye structures anterior to the lens capsule, the posterior segment being where damage from enzymatic action is most likely to occur.

The family of enzymes found particularly suitable for practice of this invention, namely the trypsin family, are characterized by molecular wieghts ranging upward from 20,000 Daltons and preferential hydrolysis of ester and peptide bonds involving the carboxyl group of basic side chain amino acids, such as arginine, and lysine. The trypsin enzymes are further characterized by possessing a serine and a histidine residue at the active center which participate in the catalytic process.

The term trypsin has been employed generically to include the whole family and such usage is intended herein. Other terms found in the literature are employed synonymously with trypsin such as for example trypsin like enzymes and acidic trypsins. In passing it may be noted that chymotrypsin is not a member of the trypsin family.

Trypsins have been isolated in pure form and characterized from widely diverse organisms, including beef, pig, sheep, human, turkeys, shark, crayfish, white shrimp, silkmoth, and even from several strains of streptomyces. The structural and functional characteristics common to the isolated trypsins have given rise to (published) theories of very remote common ancestry for the trypsin bearing gene.

In terms of practice of this invention bovine trypsin and porcine trypsin are preferred. Fortuitously, both are available in crystalline form in sufficiently high purity for pharmaceutical uses. Other trypsins are however contemplated. The trypsin component has been isolated from the proteinase mixture elaborated by *S. griseus* and tested satisfactorily for practice of this invention. For detailed description of recovery and for employment of the *S. griseus* trypsin component in practice of this invention reference is made to copending application Ser. No. 771,551 filed Feb. 24, 1977 now abandoned. Since use of the *S. griseus* trypsin is not a preferred embodiment of this invention such disclosure will not, however, be duplicated herein.

The tracking dye already alluded to as being present in the enzyme solution, 0.01–1.0% w/v must of course be of pharmaceutical grade purity. In addition, the tracking dye should, of course, be compatible with trypsin, i.e. not inhibit the trypsin, itself react with the cell tissues etc. Fluorescein has been found to be an advantageous tracking dye indicator being accepted in opthalmic practice and being available e.g. in opthalmic balanced salt solutions at concentrations e.g. 1% w/v (Alcon Laboratories) directly applicable to practice of this invention.

Preferred compositions of the present invention are then aqueous solutions of trypsin in concentrations of 0.1-10 mg/ml and of fluorescein in concentrations of 0.01-1.0% w/v. Normally the composition would be provided in separated form ready for admixture into the final composition when needed, e.g. opthalmic balanced salt solution, crystalline trypsin, opthalmic grade 1% or 10% fluorescein solution, or alternatively, crystalline trypsin and an opthalmic grade 0.1% fluorescein solution.

EXEMPLARY HANDLING AND PREPARATION OF THE ENZYMES FOR SURGICAL APPLICATION

Crystalline bovine or porcine trypsin, 42 units/mg BAEE* activity (Novo Industrie A/S) is dissolved in an opthalmic balanced salt solution pH-7.4 (Alcon) to the desired concentration, e.g. 1.2 mg/ml, the solution also containing 0.1% wt/vol of fluorescein therein. Substantial variation in trypsin concentration is possible. Acceptable test results have been obtained over the trypsin concentration range of 0.6-6.0 mg/ml.

*1 unit is defined as that amount of enzyme requiring the uptake of 1 micro-equivalent of base per minute at the following assay conditions. 0.1 M BAEE (N-benzoyl arginine ethyl ester) in Alcon opthalmic balanced salt solution pH 7.4 at 25° C.

In the instance of the trypsin fraction from *S. griseus*, the commercial proteinase ("Pronase-P," Kaken Chemical Co., Tokyo, Japan) was fractionated according to the procedure described in copending application Ser. No. 771,551 filed Feb. 24, 1977 now abandoned, and a frozen aliquot of this microbial trypsin portion (Fraction IV) thawed immediately prior to use. A sufficient volume of 1% wt./vol. solution of fluorescein in balanced salt solution (BSS) was added to the enzyme solution to make the resulting mixture 0.1% wt./vol. in fluorescein.

All enzyme solutions were subjected to cold sterilization involving millipore filtration through a 0.45 micron filter into a sterile test tube with a sterile plug top. Care was taken during handling of the enzyme to insure that all containers and apparatus coming into contact with the enzyme or liquids and substances added to the enzyme solutions were pyrogen free. After cold sterilization of the enzyme, strict aseptic techniques were used in the further handling and transfer of the enzyme. Prior to loading the enzyme in the injection apparatus, all tubing, valves, microliter syringe and cannula were chemically sterilized by ethylene oxide. The enzyme is then loaded into the assembly employing sterile techniques and the cannula is maintained in a sterile field throughout its use. Postoperatively each enzyme solution was checked for sterility via topical application of 50 μl of the solution directly from the instrument assembly onto a nutrient agar petri plate. The plates were then monitored for a period up to 10 days for evidence of microbial contamination of the hardware assembly or enzyme solution. Each enzyme solution was routinely assayed within ½ hour after its use. The presence of fluorscein has no effect upon the activity of any of the enzymes employed in this study.

SURGICAL PROCEDURE

The injection procedure is basically an atraumatic technique. The animals are placed under general anesthesia employing deep intramuscular injection of nembutal (30 mg per kilogram) and Ketamine ® (40 mg per kilogram). For a normal rabbit, it takes approximately 15 minutes for the animal to enter into deep anesthesia; and the dosage employed allows an average operating window of approximately 20 minutes. If necessary, periodic supplements of approximately 20% of the initial anesthetics dose can be given in intervals of 10 minutes apart. The pupils are dilated by topical application of 1% Mydriacyl ® and a 10% opthalmic solution of neosynephrin. One drop of each is applied to the eye every 5 minutes for a total of 3 applications. The animal is then placed upon the operating table. Strictly sterile procedures are used from this point in the operating procedure. The animal is draped and the eye irrigated with the topical opthalmic anesthetic Alcaine ®. For the rabbit, a simple spring loaded eyelid retractor is used to move the nictitating membrane away from the front of the eye. A small incision is made in the limbus with a Ziegler knife. The angle of the puncture is made nearly tangential to the radius of curvature of the cornea and the opening is so small that it can be normally observed only with the operating microscope. This type of incision is self-sealing and avoids collapse of the anterior chamber. Next a micro cannula is threaded through the incision with the aid of the operating microscope. The anterior lens capsule is then penetrated and the cannula is imbedded in or adjacent to the nucleus of the lens. A predetermined aliquot of the enzyme solution is then metered through the cannula into the lens by means of a precision microliter syringe drive assembly. Optimally for the rabbit lens, a 3-10 microliter delivery is readily contained. Following the procedure herein described, a 5 microliter delivery of 200 units/ml (based upon azo casein assay) *S. griseus* trypsin solution may be considered to be one exemplary embodiment of this invention and 5.6 microliter delivery of 1.2 mg/ml (42 units per mg based upon BAEE assay) of crystalline bovine trypsin or of crystalline porcine trypsin may be considered to be further exemplary embodiments of this invention. Direct visualization of the distribution pattern of the injected solution is achieved by incorporation of a fluorescent tracking dye, fluorescein 0.1% w/v, into the enzyme solution. After injection of the liquid, a small gas bubble, e.g., air, is introduced to seal the cavity created by the introduction of the liquid into the lens. The cannula tip is then withdrawn halfway out of the lens and the needle tract sealed with more gas, followed by further withdrawal of the cannula. The entire operation takes approximately 5 minutes. Postoperative medication consists of topical application of opthalmic Neopolycin ® ointment on the eye and intramuscular injection of a broad spectrum antibiotic (e.g., 600,000 units Bicillin ®).

Typical intralenticular incubation times for action of the digestive enzyme were two days. Thereafter, the lenses were aspirated out. Prior to aspiration of the lens, the eye is generally characterized as follows: a "ripe" eye exhibited a slightly yellow and diffuse opacity in the pupil area region resulting from liquefaction of lens tissue and of denaturation of lens proteins within the subcapsular region and re-distribution of the tracking dye throughout the intralenticular volume. Considering the ease with which the rabbit eye is traumatized, the eyes were "quiet" and exhibited only very minor response postoperatively to the enzyme injection.

For aspiration of the lens, the animals were again placed under general anesthesia initially employing the standard quantity of anesthetics described above but supplemented with an extra 50% of each anesthetic after 10 minutes. The pupils are again dilated by application of Mydriacyl ® and neosynephrine. The animal was placed upon the operating table and draped with strict sterile procedure used thereafter. A 2-3 millimeter incision is made in the limbus with a Ziegler knife. The anterior capsule is then ruptured by means of a sharp needle to expose the liquefied lens. Small amounts of fibrin plaque which are sometimes formed in the anterior chamber of the rabbit eye are easily removed with microforceps and then the lens is aspirated out. The aspiration/irrigation device used is a commercially available aspiration/irrigation assembly. The irrigation fluid employed was either sterile lactated Ringer's solution (Abbott Laboratories) or an opthalmic grade of balanced salt solution (Alcon Laboratories). The intralenticular aspiration of softened lens material is optimally performed employing the operating microscope as a viewing aid. After aspiration, the incision in the limbus is closed with 1-3 sutures and the anterior chamber reformed. Postoperative medication consists of 0.25 ml of an opthalmic preparation of Celestone ® applied subconjuctively, Neopolycin ® ointment topically, and a broad spectrum antibiotic intramuscularly (Bicillin ® 600,000 units). The animals were given daily applications of dilating drops consisting of an opthalmic solution of atropine sulfate, neosynephrin and Maxitrol ® to minimize synechia formation. Actual operating time from opening to closing of the eye is approximately 15-20 minutes.

Best results were obtained with enzyme dosages for the rabbit eye of 3-10 microliters of an enzyme solution containing 50-500 units/ml activity (based upon an azocasein assay) for the S. griseus trypsin and 25-250 units/ml activity (based upon a BAEE assay) for porcine and bovine trypsins, with introduction of the enzyme solution split, half into one portion of the lens and half into another portion of the lens. Experience with albino rabbits with the above dosage range, indicated that a two day incubation period softens the lens enough for removal by aspiration. In several instances the operation on the rabbit was so successful that both anterior capsule and posterior capsule were completely intact with the exception of the incision made in the anterior capsule to allow entry of the aspiration needle. In several of the rabbits, the lens aspirated eye was practically indistinguishable from the control eye (to lateral visual examination).

A like series of tests were performed on pigmented rabbits and on cats. Overall, the results of the operation for pigmented rabbits were identical to the observations and experiences with the albino rabbit. In the case of the cats, the results were qualitatively similar to that of the rabbits, being different in detail due to the fact that the cat nucleus is an extremely hard, dense matrix and very characteristic of that found in the hard, bruescent human cataract. When enzyme dosages similar to those used for the rabbit were employed for the cat, complete softening of the nucleus was not achieved. Because of the extreme density of the cat nucleus, the injected enzyme was initially distributed within the softer cortical region and digestion of the nuclear region occurred first at the periphery and then toward the center. Upon aspiration of the peripheral portions of the cat lens, there was observed a small dense pocket of remaining nuclear material from the center of the lens which was approximately ⅓ the diameter of the normal, compact cat nucleus. Although this nuclear material could not be aspirated, it was small enough to be easily removed through the incision in the limbus. Therefore, in the case of extremely large and dense nuclear regions such as those found in the cat eye, higher enzyme dosages and longer intralenticular incubation times will be needed relative to those employed for the rabbit model.

One last point should be made regarding the formation of fibrin in the anterior chamber for both cat and rabbit. In both animals, formation of fibrin is a common post operative phenomenon. This phenomenon does not occur in humans, as the aqueous does not contain substantial amounts of clotting proteins as is the case with both rabbit and cat. In the case of the rabbit, the formation of fibrin postoperatively was observed on a sporadic basis and in a number of cases, the fibrin clots spontaneously redissolved.

More details as to exemplary test studies are provided below. The enzyme solutions were injected into the rabbit lens. All enzyme solutions contained about 0.1% w/v of fluorescein.

54 eyes were injected 102 times with no posterior capsule breakthrough.

ENZYME #1—Bovine Trypsin (crystalline NOVO)

| Concentration | Vol. | Observations Post Injection |
| --- | --- | --- |
| 0.6 mg/ml | 5.6 μl | Moderately soft |
| 0.8 mg/ml | 5.6 μl | cortex with hard |
| 1.0 mg/ml | 5.6 μl | nucleus |
| 1.2 mg/ml | 5.6 μl | Soft cortex with |
| 1.4 mg/ml | 5.6 μl | relatively soft nucleus |
| 1.5 mg/ml | 5.6 μl | |
| 1.6 mg/ml | 5.6 μl | Very soft cortex with |
| 2.0 mg/ml | 5.6 μl | soft nucleus |

ENZYME #2—Porcine Trypsin (crystalline NOVO)

| Concentration | Vol. | Observations - Post Injection |
| --- | --- | --- |
| 0.6 mg/ml | 2.8 and 5.6 μl | Moderately soft cortex |
| 0.8 mg/ml | 5.6 μl | with hard nucleus |
| 0.9 mg/ml | 5.6 μl | |
| 1.0 mg/ml | 5.6 μl | |
| 1.2 mg/ml | 5.6 μl | Soft cortex with |
| 1.5 mg/ml | 5.6 μl | relatively soft nucleus |
| 3.0 mg/ml | 5.6 μl | Very soft cortex with |
| 6.0 mg/ml | 5.6 μl | soft nucleus |

TRAUMA STUDIES—ANTERIOR SEGMENT

A study was made to determine if there is any gross pathological effect of the enzymes upon any anterior segment structures of the eye or related physiological functions. Such study approximates the accidental exposure of the anterior segment to the lens liquefying enzyme or egress of the enzyme after placement within the lens into the anterior segment of the eye.

For details of the experimental techniques employed in this trauma study, reference is made to copending application Ser. No. 771,551 filed Feb. 24, 1977 now abandoned.

Introduction of bovine trypsin, porcine trypsin, and the microbial trypsin of Fraction IV isolated from the S. Griseus preparation "Pronase" into the anterior segment of the rabbit eye did not cause significant trauma in the eye.

TRAUMA STUDIES—POSTERIOR SEGMENT

The purpose of this study was to ascertain what, if any, effect the lens liquefaction enzymes have upon posterior segment structures of the eye. This study was intended to evaluate possible trauma resulting from the accidental placement or egress of the trypsin from within the lens capsule into the posterior segment.

For details of the experimental techniques employed in the posterior segment trauma studies, reference is made again to Ser. No. 771,551 filed Feb. 24, 1977 now abandoned.

Introduction of bovine trypsin, porcine trypsin, and the microbial trypsin of Fraction IV isolated from the *S. Griseus* preparation of "Pronase" into the posterior segment of the rabbit eye caused discernable pathological trauma thereto in each instance. This study indicates that care should be taken to avoid introduction of the enzyme into the posterior segment. This study also evidences that enzyme introduced into the lens remains compartmentalized therein.

What is claimed:

1. A method for enzymatically treating cataracts in vivo which comprises injecting a concentrated solution of a trypsin directly into the lens of an eye, then allowing enzymatic digestion of the lens to take place and thereafter removing the enzyme digested lens material.

2. The method of claim 1 wherein a tracking indicator is included in the enzyme solution.

3. The method of claim 1 wherein the trypsin is bovine trypsin.

4. The method of claim 1 wherein the trypsin is porcine trypsin.

5. The method of claim 1 wherein said removal is by irrigation and aspiration.

6. The method of claim 1 wherein the trypsin concentration is 0.1–10 mg/ml.

7. The method of claim 1 wherein the trypsin concentration is 0.1–10 mg/ml and wherein 0.01–1.0% w/v of fluorescein is present in the solution.

* * * * *